Nov. 4, 1952 J. PARMENTIER Plant Pat. 1,142
ROSE PLANT
Filed Nov. 21, 1951
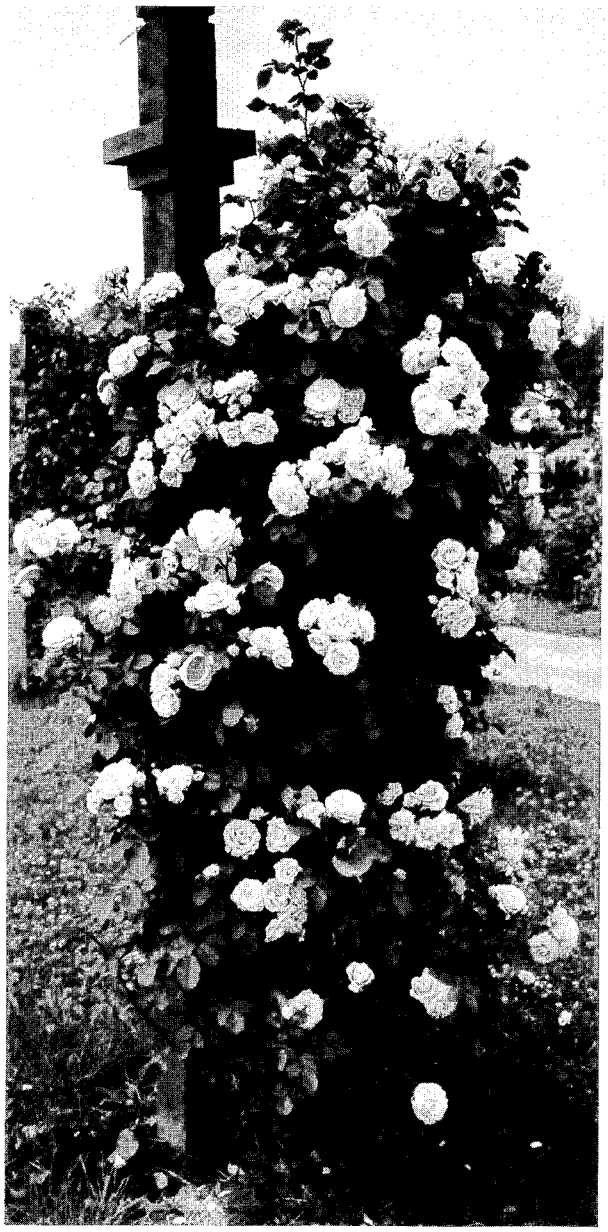
Inventor.
John Parmentier
By: Robert Cobb
attorneys.

Patented Nov. 4, 1952

Plant Pat. 1,142

UNITED STATES PATENT OFFICE 1,142

ROSE PLANT

John Parmentier, Bayport, N. Y., assignor to Jackson & Perkins Company, Newark, N. Y., a corporation of New York Application November 21, 1951, Serial No. 257,443

1 Claim. (Cl. 47—61)

The present invention relates to a new and distinct variety of rose plant of the climber class, originating as a sport of the Floribunda bush rose variety "Pinocchio" (Plant Patent No. 484). The new variety was discovered by me amongst cultivated plantings on my property at Bayport, Long Island, New York.

This new variety has substantially the same general form and color of its foliage and flowers as its parent "Pinocchio," but is very vigorous, upright and branching in its habits of growth, sending up long basal shoots 6 to 8 feet tall the first year, and which in turn send out lateral blooming spikes continuously throughout the summer season. The flowers are Geranium Pink in general color tonality, showing a light cast of Light Orange-Yellow from the base, particularly in the early blooming season, as typical of "Pinocchio," and the flowers are borne in repeating clusters occurring on the end of the tall basal shoots and on the side branches thereof throughout the entire summer, which is unusual in pink climbing roses.

Asexual reproduction of this new variety by budding at Newark, New York, and at Pleasanton, California, shows that the foregoing characteristics come true to form and are established and transmitted through succeeding propagations.

The accompanying drawing shows a typical specimen plant of the new variety as observed in the garden at Newark, New York, about midmorning in the month of July, and illustrates its climbing habit of growth and its cluster habit of bloom as hereinbefore described.

A more detailed description of the form and color of the foliage and flowers of the new variety may be had from reference to Plant Patent No. 484, and therefore these details need not be repeated herein.

I claim:

A new and distinct variety of rose plant of the climber class, substantially as herein shown and described, characterized as to novelty by its similarity in general form and color of its foliage and flowers to those of its parent "Pinocchio" (Plant Patent No. 484), but dominantly distinguished therefrom by its vigorous, climbing, upright, branching habits of growth, and by bearing its flowers in repeating clusters on the end of tall basal shoots and on side branches thereof, repeating throughout the summer season.

JOHN PARMENTIER.

No references cited.